(12) United States Patent
Haraldsted et al.

(10) Patent No.: US 11,097,046 B2
(45) Date of Patent: Aug. 24, 2021

(54) MEDICAL INJECTION DEVICE WITH A CLEANING CHAMBER

(71) Applicant: Novo Nordisk A/S, Bagsvaerd (DK)

(72) Inventors: Mie Haraldsted, Helsingoer (DK); Morten Revsgaard Frederiksen, Copenhagen K (DK); Matias Melander, Copenhagen (DK); Christian Hoejris Nielsen, Copenhagen NV (DK); Graham Hinde, Eindhoven (NL); Bas Kamp, Eindhoven (NL); Roshan Hakkim, Eindhoven (NL)

(73) Assignee: Novo Nordisk A/S, Bagsvaerd (DK)

( * ) Notice: Subject to any disclaimer, the term of this patent is extended or adjusted under 35 U.S.C. 154(b) by 175 days.

(21) Appl. No.: 15/754,332

(22) PCT Filed: Aug. 10, 2016

(86) PCT No.: PCT/EP2016/069004
§ 371 (c)(1),
(2) Date: Feb. 22, 2018

(87) PCT Pub. No.: WO2017/032599
PCT Pub. Date: Mar. 2, 2017

(65) Prior Publication Data
US 2018/0243498 A1  Aug. 30, 2018

(30) Foreign Application Priority Data

Aug. 25, 2015 (EP) ..................................... 15182290

(51) Int. Cl.
*A61M 5/32* (2006.01)
*A61M 5/00* (2006.01)
(Continued)

(52) U.S. Cl.
CPC ............ *A61M 5/001* (2013.01); *A61M 5/286* (2013.01); *A61M 5/31573* (2013.01);
(Continued)

(58) Field of Classification Search
CPC .. A61M 5/001; A61M 5/31573; A61M 5/326; A61M 5/3271; A61M 5/3257;
(Continued)

(56) References Cited

U.S. PATENT DOCUMENTS 2,888,924 A * 6/1959 Dunmire ............... A61M 5/282
604/196
3,354,881 A    11/1967 Bloch
(Continued)

FOREIGN PATENT DOCUMENTS

CN        101171044 A      4/2008
CN        102481417 A      5/2012
(Continued)

*Primary Examiner* — Deanna K Hall
(74) *Attorney, Agent, or Firm* — Wesley Nicolas

(57) ABSTRACT

The invention relates to an injection device for injecting a liquid drug. The injection device comprises a housing assembly supporting a non-removable cartridge having an interior chamber containing the liquid drug to be injected and a reusable needle cannula connected to the cartridge. A needle shield assembly provided with a cleaning chamber containing a volume of a cleaning agent for cleaning at least the distal tip of the needle cannula between subsequent injections is further provided. The needle shield assembly is axially movable in a proximal direction in relation to the housing assembly from a first position to a second position upon rotation of at least a part of the needle shield assembly, wherein the first position is a position in which the distal tip of the needle cannula is located inside the cleaning chamber thereby cleansing the distal tip of the needle cannula, and the second position is a position in which the distal tip of the (Continued)

needle cannula is located outside and distal to the cleaning chamber for equalizing the pressure in the cartridge.

14 Claims, 7 Drawing Sheets

(51) Int. Cl.
  *A61M 5/315* (2006.01)
  *A61M 5/28* (2006.01)
  *A61M 5/20* (2006.01)

(52) U.S. Cl.
  CPC .......... *A61M 5/326* (2013.01); *A61M 5/3257* (2013.01); *A61M 5/3271* (2013.01); *A61M 2005/2073* (2013.01); *A61M 2005/3267* (2013.01); *A61M 2005/3284* (2013.01)

(58) Field of Classification Search
  CPC .......... A61M 5/286; A61M 2005/3284; A61M 2005/2073; A61M 2005/3267; A61M 5/19; A61M 5/31596; A61M 2005/1787; A61M 5/284; A61M 5/3272; A61M 5/3202; A61M 5/3243; A61M 2205/60
  See application file for complete search history.

(56) References Cited

U.S. PATENT DOCUMENTS

| | | | |
|---|---|---|---|
| 4,416,663 A | * | 11/1983 | Hall .............. A61M 5/326 604/198 |
| 4,507,118 A | | 3/1985 | Dent |
| 4,666,436 A | | 5/1987 | McDonald et al. |
| 5,312,347 A | | 5/1994 | Osborne et al. |
| 5,383,862 A | | 1/1995 | Berndt et al. |
| 5,591,138 A | * | 1/1997 | Vaillancourt ....... A61M 5/3271 604/192 |
| 8,216,193 B2 | | 7/2012 | Rolla |
| 9,072,841 B2 | | 7/2015 | Thueer et al. |
| 9,138,546 B2 | | 9/2015 | Schubert et al. |
| 9,789,264 B2 | | 10/2017 | Roberts et al. |
| 10,463,798 B2 | | 11/2019 | Kosinski et al. |
| 2005/0142180 A1 | * | 6/2005 | Bisgaier ............. A61K 38/1709 424/450 |
| 2008/0262436 A1 | * | 10/2008 | Olson ................ A61M 5/3202 604/198 |
| 2011/0118667 A1 | * | 5/2011 | Zaiken ................ A61M 5/326 604/138 |
| 2012/0123350 A1 | * | 5/2012 | Giambattista ....... A61M 5/2033 604/198 |
| 2014/0276450 A1 | * | 9/2014 | Bendix ............. A61M 5/31551 604/207 |

FOREIGN PATENT DOCUMENTS

| CN | 103108666 A | 5/2013 |
|---|---|---|
| CN | 103228306 A | 7/2013 |
| EP | 0409180 A1 | 1/1991 |
| RU | 2009126085 A | 1/2011 |
| WO | 8802638 A1 | 4/1988 |
| WO | 2014029018 A1 | 2/2014 |
| WO | 2014037323 A1 | 3/2014 |
| WO | 2014064100 A1 | 5/2014 |
| WO | 2014068098 A1 | 5/2014 |
| WO | 2015062845 A1 | 5/2015 |

* cited by examiner

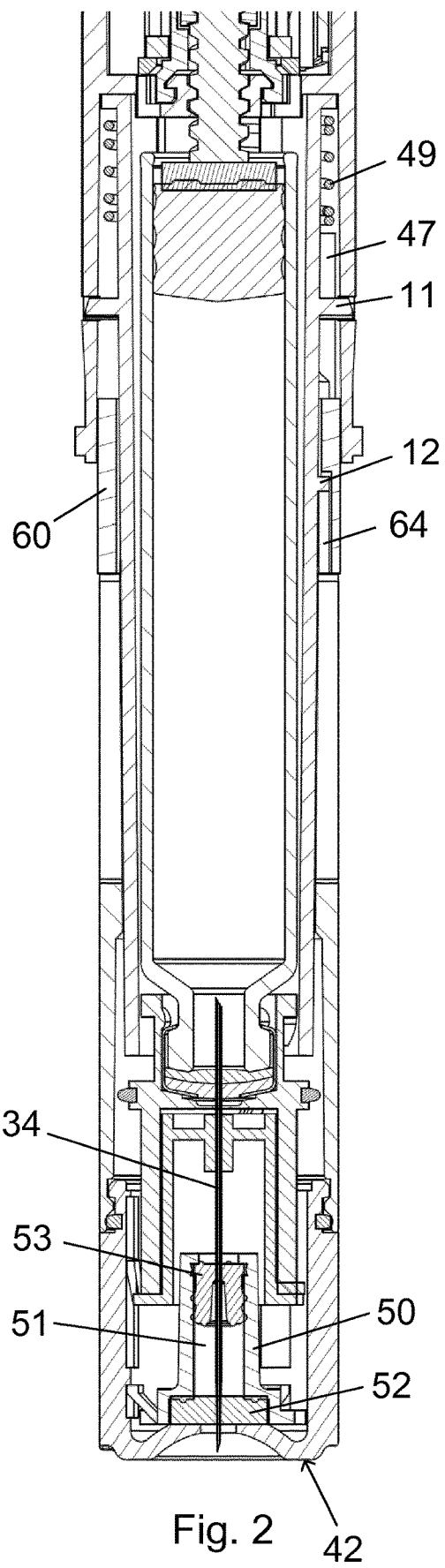
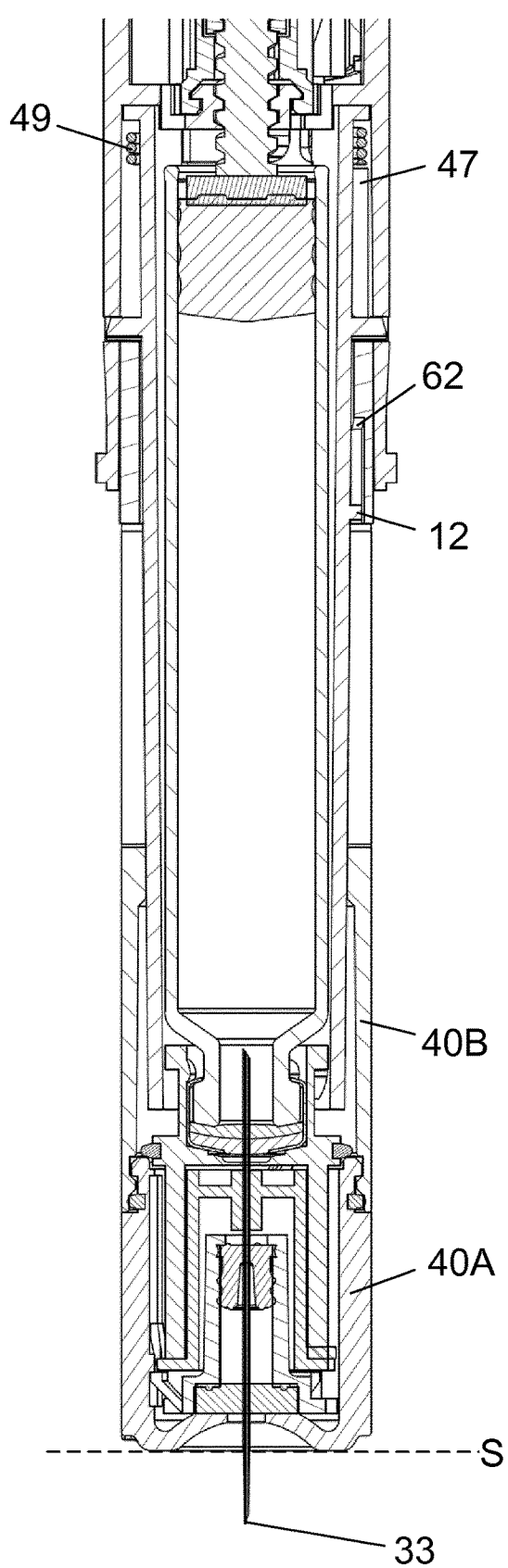
Fig. 2
Fig. 3

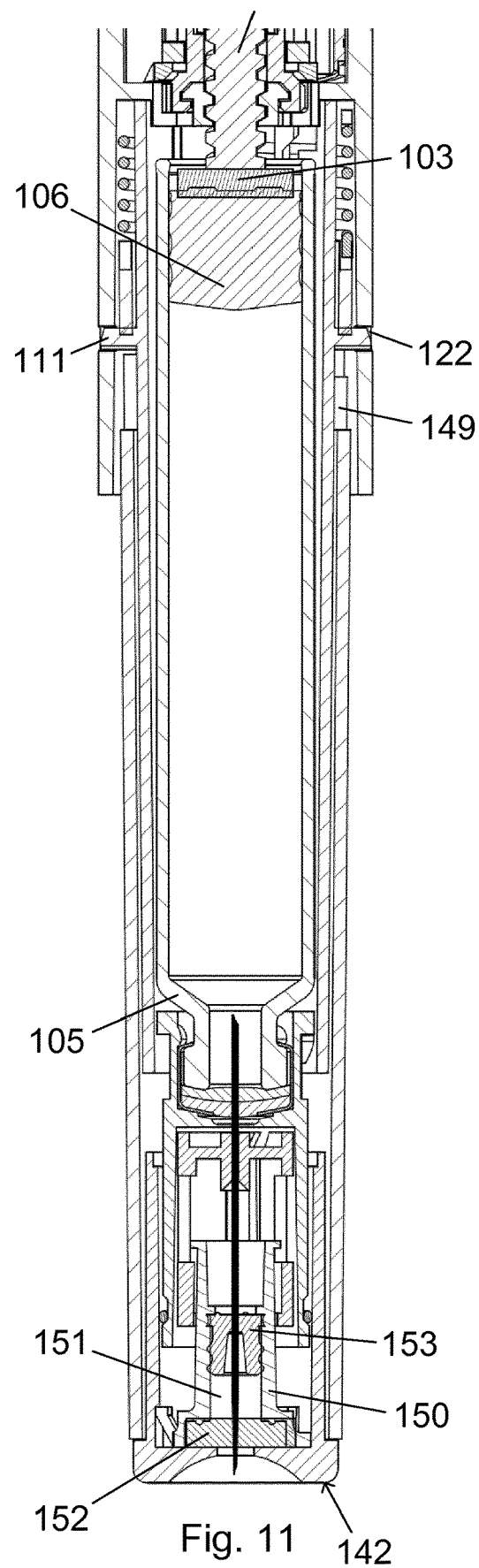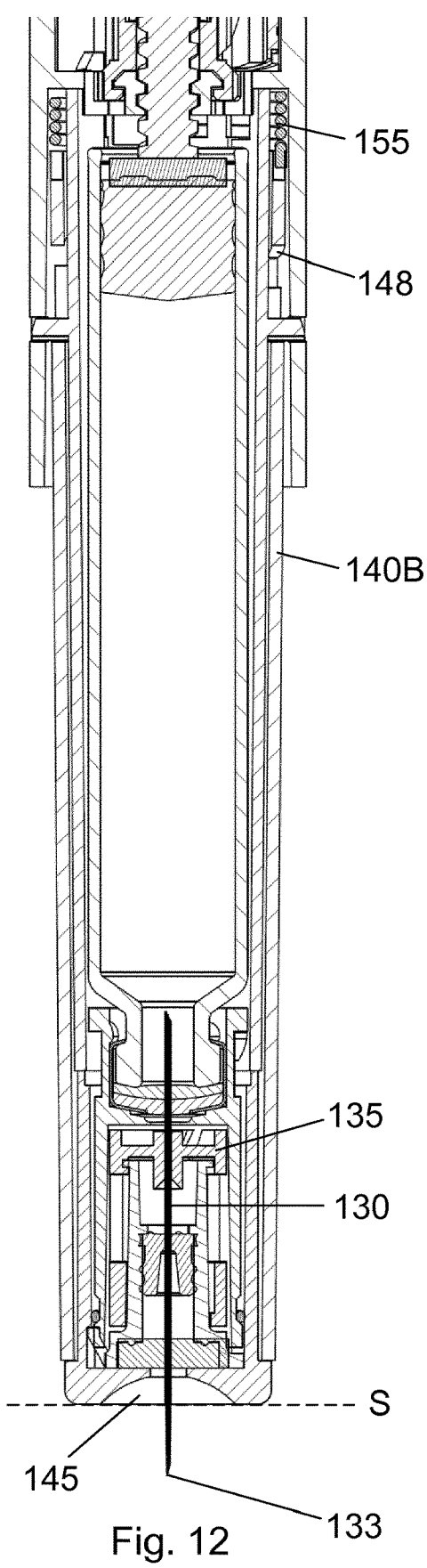

Shield in first position

Shield in second position

MEDICAL INJECTION DEVICE WITH A CLEANING CHAMBER

CROSS-REFERENCE TO RELATED APPLICATIONS

This application is a 35 U.S.C. § 371 National Stage application of International Application PCT/EP2016/069004 (published as WO 2017/032599), filed Aug. 10, 2016, which claims priority to European Patent Application 15182290.5, filed Aug. 25, 2015, the contents thereof which are incorporated by reference in their entirety.

THE TECHNICAL FIELD OF THE INVENTION

The invention relates to a medical injection device for injecting a liquid drug and especially to a pre-filled injection device for apportioning a multiple number of doses, the doses preferably being individual settable by the user. The invention especially relates to such pre-filled injection device wherein the same needle cannula is used for a multiple number of injections and wherein the tip of the needle cannula is cleaned between subsequent injections.

DESCRIPTION OF RELATED ART

Injection devices wherein the tip of the needle cannula is maintained in a cleaning solvent between subsequent injections are disclosed in U.S. Pat. Nos. 3,354,881, 4,416,663 and in U.S. Pat. No. 4,666,436. As can be seen from these prior art injection devices, the cleaning chamber is usually carried on a retractable needle shield covering the distal tip of the needle cannula between subsequent injections.

Further WO2014/064100 discloses a pre-filled disposable injection device which has a telescopically shield covering the distal tip of the needle cannula between subsequent injections. This telescopically shield is urged into a distal covering position by a spring. Further, in one embodiment, the shield is provided with a hollow chamber containing a liquid solvent such as a chemical disinfectant or biocide which cleans the tip of the needle cannula between subsequent injections.

Examples on such cleaning solvents are provided in WO 2014/029018. However, as disclosed in WO 2015/062845 it is preferred to use the preservative contained in the liquid drug as the cleaning solvent. This can e.g. be done by filling the cleaning chamber with preservative containing liquid drug directly from the cartridge and thus use a quantum of the preservetive containing liquid drug itself as the cleaning solvent.

However, when filling the cleaning chamber with preservative containing liquid drug from the cartridge there is a risk of creating an overpressure inside the liquid system which comprises the interior space of the cartridge, the lumen of the needle cannula and the cleaning chamber which together forms a closed liquid system.

Further, no matter which cleaning agent is used there is always a risk of an overpressure being build up inside the liquid system especially due to temperature changes in the liquid drug caused by different storing conditions for the injection device.

Such overpressure in the liquid system and especially inside the cartridge can have the unfortunate effect that the liquid volume ejected is larger than the volume (the doses) set by the user.

It is therefore important to equalize the pressure in the liquid system or at least in the cartridge prior to making an injection. Otherwise the dose size expelled can be different from the set and intended dose due to these pressure differences.

DESCRIPTION OF THE INVENTION

It is thus an object of the present invention to provide an injection device in which any overpressure in the liquid system can be easily vented prior to performing an injection.

Accordingly, in one aspect, the present invention relates to an injection device for injecting a liquid drug. The injection device comprises:
- a housing assembly supporting a non-removable cartridge having an interior chamber containing the liquid drug to be injected: The housing assembly can be assembled from several parts which together makes up an outer shell of the injection device,
- a needle cannula which is connected to the interior of the cartridge at least during injection and which needle cannula has a longitudinal lumen through which the liquid drug flows during injection and which lumen connects a distal part of the needle cannula having a distal tip with a proximal part of the needle cannula,
- a needle shield assembly which is provided with a cleaning chamber containing a volume of a cleaning agent for cleaning at least the distal tip of the needle cannula between subsequent injections.

Further, the needle shield assembly is movable in a proximal direction in relation to the housing assembly from a first position to a second position.

The first position being a position in which the distal tip of the needle cannula is located inside the cleaning chamber, and the second position being a position in which the distal tip of the needle cannula is located outside and distal to the cleaning chamber and the needle shield assembly is movable from the first position to the second position upon rotation of at least a part of the needle shield assembly.

The needle shield assembly is preferably made up from a number of parts whereof one or more parts are rotatable relatively to the housing. The other parts not being rotatable in relation to the housing assembly can be axially connected to the rotating part or parts such that the non-rotating parts moves axially together with the rotating part but do not rotate together with the rotating part or parts.

Thus upon rotation of at least a part of the needle shield assembly i.e. as a consequence of rotating the at least one part of the needle shield assembly, the needle shield assembly moves from the first position to the second position such that at least the distal tip of the needle cannula is moved outside the cleaning chamber and exposed to the surroundings.

The liquid system comprises at least the interior of the cartridge, the lumen of the needle cannula and the interior of the cleaning chamber. Once the distal tip of the needle cannula is brought to a position just distal to the cleaning chamber, any overpressure present at least inside the cartridge and in the lumen of the needle cannula will equalize with the pressure of the surroundings.

Any overpressure present inside the cleaning chamber will not be equalized at once by exposing the distal tip of the needle cannula, but once the distal tip of the needle cannula is moved back into the cleaning chamber such overpressure will equalise with the pressure inside the cartridge and after the distal tip of the needle cannula has been moved in and out of the cleaning chamber a few number of times any overpressure present in the cleaning chamber will slowly disappear. Further, an overpressure inside the cleaning chamber does not influence on the dose sizes as the distal tip of the needle cannula is moved directly from the exposed position and into the skin of the user during injection.

Further a part of the needle shield assembly is helically guided in relation to the housing assembly such that when the user rotates the specific part of the needle shield assembly it performs a helical movement in relation to the housing assembly.

The needle shield assembly is preferably made up from a number of different parts which together forms the needle shield. Once the entire needle shield or at least a part of the needle shield is rotated it is thus guided helically in the proximal direction such that the needle shield or the part of the needle shield moves proximally in order to expose the distal tip of the needle cannula in front of the needle shield.

The helical guidance is preferably created by having one of the needle shield assembly or the housing assembly to be provided with a protrusion and the other of the needle shield assembly or the housing assembly to be provided with a helical track. The protrusion thus operates in the helical track, such that at the least one part the needle shield assembly move helically in relation to the housing assembly upon rotation of the at least one part of the needle shield assembly relatively to the housing assembly.

Only one single protrusion and one helical track are needed in order to secure the helical guidance. However, any number of protrusions and helical tracks can be provided.

The helical track in which the protrusion is guided preferably terminates into an axial track allowing the needle shield assembly to be moved in the proximal direction during expelling of the set dose. Once the needle shield assembly or the part of the needle shield assembly has been rotated through the helical track and into the axial track, the needle shield assembly is able to move in a straight axial direction following the axial track. The needle shield assembly can further be provided with a "parking position" in which it is not possible to move the needle shield assembly in the axial direction at all. When not in this "parking position", the needle shield assembly or part thereof is bound to move helically until the protrusion enters into the axial track. Only when the protrusion is positioned in the axial track, the needle shield can move purely axially and not helically.

As a consequence the user thus has to rotate the needle shield assembly or part thereof before it is possible to perform an injection.

In order to return the needle shield after an injection has been performed, a compression spring is operational provided between the needle shield assembly and the housing assembly. This compression spring can be any kind of spring providing an axial force. The spring can made from either steel or a polymeric material, it can in one example be moulded as a part of the needle shield assembly. However, the spring does not necessarily have to abut neither the needle shield assembly nor the housing assembly, it merely has to operate between the needle shield assembly and the housing thus moving these parts away from each other.

The needle shield assembly can be assembled from any number of individual parts, however in the disclosed two embodiments the needle shield assembly comprises a distal shield part and a proximal shield part which are rotatable in unison.

In one example, the needle shield assembly also comprises a rotatably ring which is connected to the remaining parts of the needle shield assembly such that these parts travels axially together with the rotatable ring but without rotating.

In one specific example the rotatable ring is rotatable in relation to the proximal shield part but axially secured to the proximal shield part. The rotatable ring whenever guided for helical movement in relation to the housing assembly thus brings the proximal shield part along with it in the axial direction but without transferring rotation to the proximal shield part.

In a specific example the helical movement of the rotatable ring is introduced by providing either the rotatable ring or the housing assembly with a protrusion and the other of the rotatable ring or the housing assembly with a helical track. The protrusion can be shaped as a thread segment to further provided a helical guidance.

In a different example a helical rotation of the needle shield assembly is introduced by providing the needle shield assembly or the housing assembly with a protrusion and the other of the needle shield assembly or the housing assembly with a helical track such that the needle shield assembly move helically in relation to the housing assembly upon rotation of the needle shield assembly relatively to the housing assembly.

In the latter example the needle shield assembly is provided with a window and the housing assembly is provided with an opening. When the user thus rotate the needle shield assembly to equalize the pressure, the window is brought into alignment with the opening which in the second position of the needle shield assembly makes it possible for the user to inspect the liquid drug in the cartridge.

Both the window in the needle shield assembly and the opening can have any shape but when implemented in a longitudinal pen-shaped injection device, the window is preferably a longitudinal window and the opening is thus made to accommodate the window.

Henceforth, as the needle shield assembly is rotated into the second position, the longitudinal window is brought into alignment with the longitudinal opening of the cartridge holder which gives the user the possibility to view the cartridge or at least part of the cartridge and thus the content of the cartridge which gives the user an indication that the pressure has been equalized. Further, in this second position the needle shield assembly is free to move in the proximal direction thus it is only possible to perform an injection after having rotated the needle shield assembly. The indication given by the alignment of the longitudinal window with the longitudinal opening is henceforth further an indication that the injection device is unlocked and ready to inject.

In a further example, the cleaning chamber is provided in a cleaning unit which is carried by the needle shield assembly. When manufactured as a cleaning unit it can be properly sterilized and handled separately thereby providing excellent manufacturing options.

The cleaning agent contained in the cleaning chamber can be any kind of liquid that is able to rinse the distal tip of the needle cannula from bacteria and which prevents the further growth of bacteria. In one example the cleaning agent could be an alcohol, however in order to minimize the risk of contaminating the liquid drug in the cartridge by cleaning agent flowing through the lumen of the needle cannula and into the cartridge it is preferred to use a preservative already present in the liquid drug formulation. A suitable cleaning agent would therefore be phenol or meta-cresol which are broadly used as preservatives in liquid drugs.

In one specific example, the liquid drug, when containing a preservative, can be used as the cleaning agent as disclosed in WO 2015/062845.

The distal end surface of the needle shield assembly is preferably provided with a countersunk opening or a recess such that the distal tip of the needle cannula can be concealed in a position inside this countersunk opening or recess during equalizing of the pressure. The user is then able to lay the distal end surface of the needle shield assembly on the surface of the skin without the distal tip of the needle cannula touching the surface of the skin. Only as the user presses the injection device against the skin with a certain force will the needle shield assembly slide in the proximal direction and the needle cannula penetrate the skin.

The force needed to move the needle shield assembly is mainly determined by the force of the compression spring urging the needle shield in the distal direction.

In a further example the countersunk area or recess is formed as a concave recess preferably surrounding an opening through which the needle cannula can pass. The opening is preferably made with a rather narrow diameter such that the distal tip of the needle cannula is prevented from passage if bended.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle all though the needle cannula could also be connected directly to the housing structure without using a needle hub As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container rigid or flexible can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

"Cleaning chamber" is in the present description broadly meant to be any kind of reservoir containing a cleaning solvent to clean at least the distal tip of the needle cannula between subsequent injections. Such cleaning chamber is preferably both distally and proximally sealed by a pierceable septum. However, the pierceable septums could be replaced by any kind of sealing which would seal against the outer surface of the needle cannula. The distal septum and the proximal septum or seal of the cleaning chamber defines a confinement containing the cleaning solvent which cleaning solvent in a preferred embodiment is identical to the preservatives contained in the liquid drug used in the specific injection device. In a most preferred solution, the same preservative containing liquid drug is present in both the cleaning chamber and in the cartridge of the injection device thereby avoiding contamination of the preservative containing drug inside the cartridge.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" as used in this description is intended to mean that the parts, which in this application is embodied as a cartridge and a needle assembly, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 2 show the cross sectional view of the distal part of the injection device with the needle shield in the second position.

FIG. 3 show a cross sectional view of the distal part of the injection device during injection.

FIG. 11 show a cross sectional view of the distal part of the injection device according to another embodiment with the needle shield in the second position.

FIG. 12 show a cross sectional view of the distal part of the injection device according to another embodiment during injection.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying a dose dial button.

Distal and proximal are meant to be along an axial orientation extending along the longitudinal axis "X" of the injection device and is further indicated in the figures.

First Embodiment

Figure 1:
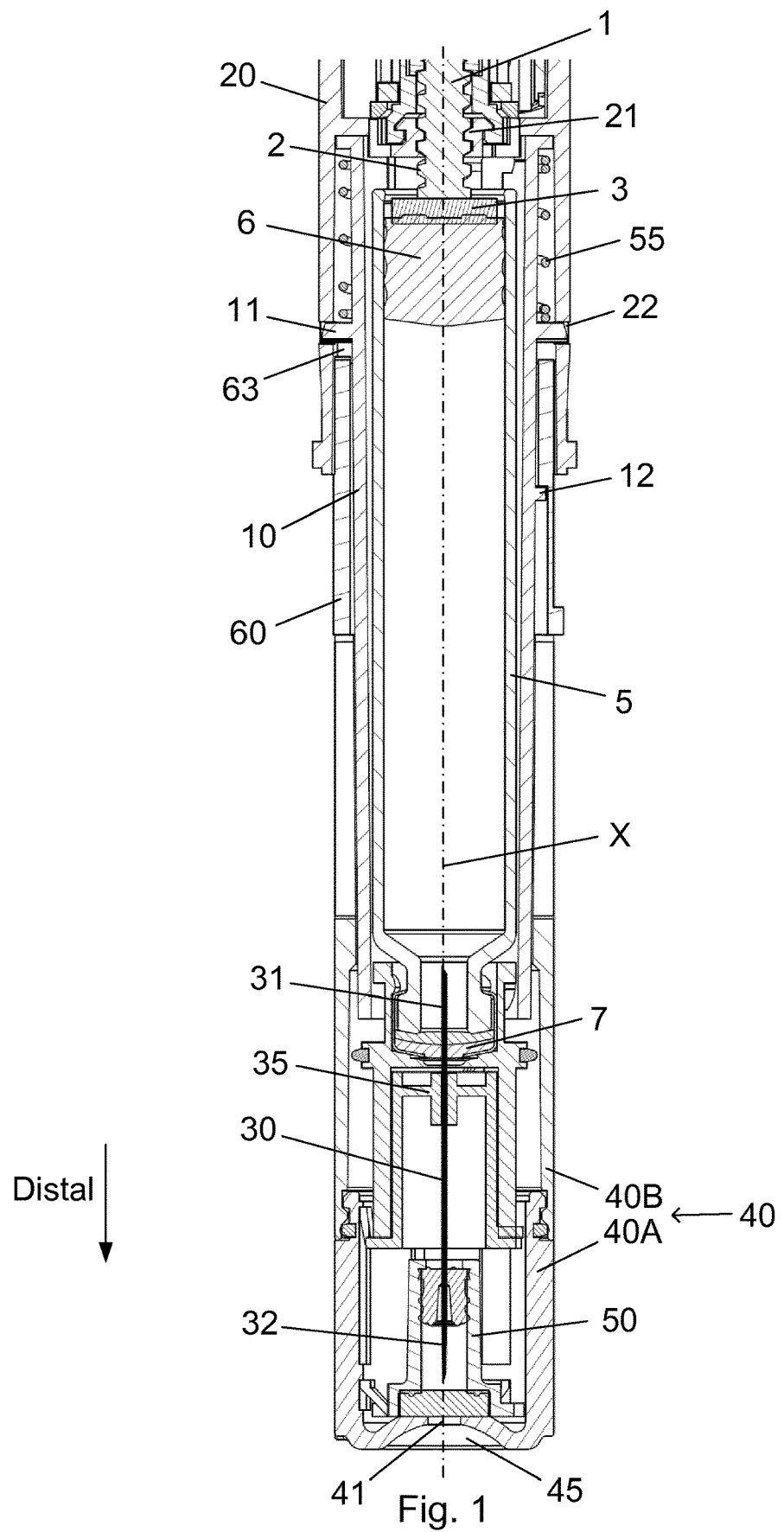
FIG. 1 show a cross sectional view of the distal part of the injection device with the needle shield in the first position.

The distal part of the injection device is disclosed in the FIGS. 1 to 3. A cartridge 5 containing the liquid drug to be expelled is secured in a cartridge holder 10 which is coupled to the housing 20.

The cartridge 5 is proximally sealed by a movable plunger 6 and distally closed by a pierceable septum 7.

The housing 20 proximally encapsulates the dose setting and injection mechanism which comprises a drive mechanism for driving forward a piston rod 1. The piston rod 1 is distally provided with a piston rod foot 3 which abuts a plunger 6 provided inside the cartridge 5. The piston rod 1 has an outer thread 2 which is engaged by a similar thread 21 formed in the housing 20 such that the piston rod 1 is moved helically whenever the piston rod 1 is rotated.

The cartridge holder 10 which internally secures the cartridge 5 is secured to the housing 20 by having a plurality of outwardly pointing protrusions 11 engaging openings 22 provided in the housing 20. The cartridge holder 10 is thus both rotational and axially locked to the housing 20 and could alternatively be formed as an integral part of the housing 20. Henceforth the cartridge holder 10 could in many aspects be considered a part of the housing 20 here after referred to as a housing assembly 10, 20.

As depicted in FIG. 1, a needle cannula 30 is penetrated through the pierceable septum 7 of the cartridge 5. The needle cannula 30 has a proximal part 31 inserted into the cartridge 5 and a distal part 32 with a sharp tip 33 for penetrating the skin (S) of user during injection (FIG. 3). Once the proximal part 31 has penetrated through the septum 7 and into the cartridge 5, the liquid drug can flow through the lumen 34 of the needle cannula 30.

The needle cannula 30 is secured in a hub 35 which can be axially moved during initiation of the injection device as e.g. disclosed in PCT application No. PCT/EP2016/057233.

Figure 4:
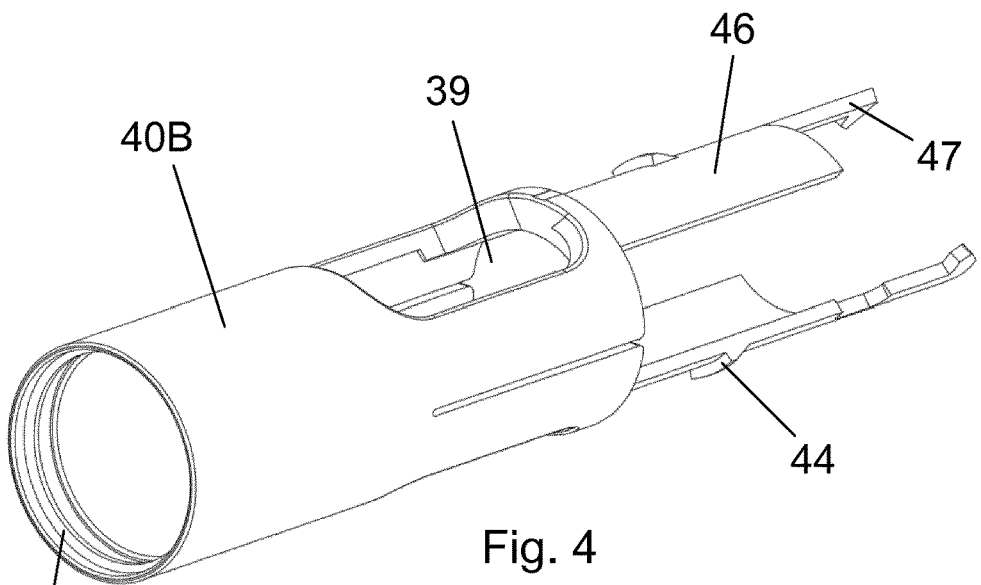
FIG. 4 show a perspective view of a part of the needle shield assembly.

Further, the distal tip 33 of the needle cannula 30 is hidden by an axially movable needle shield assembly 40. In the first embodiment depicted in the FIGS. 1 to 7, the needle shield assembly 40 is assembled from two parts, a distal shield part 40A and a proximal shield part 40B. However, the needle shield assembly 40 could easily be moulded as one unitary part. As best seen in FIG. 4, the proximal shield part 40B has a circumferential track 43 provided on the inside of the distal end for securing therein the distal shield part 40A such that the distal shield part 40A and the proximal shield part 40B operates as one needle shield assembly 40.

The proximal shield part 40B is further provided with two proximal extending axial extensions 46 which terminate in proximally pointing arms 47. These two arms 47 are preferably provided with a radial extension at their respective proximal ends. These radial extensions abut a compression spring 55 which proximally abuts the housing 20 (e.g. via the cartridge holder 10 as depicted in FIGS. 1 to 3). The proximal extensions 46 are further provided with an outwardly pointing protrusion 44 for axially securing a rotatable ring 60 as will be explained.

The distal shield part 40A is distally provided with an opening 41 through which the needle cannula 30 can penetrate as disclosed in FIGS. 2 and 3. The most distal surface 42 of the distal shield part 40A is further provided with a concave recess 45 such that the distal tip 33 of the needle cannula 30 can be brought to a position outside the cleaning chamber 51 but still within the boundaries of the distal shield part 40A, the function of which will be apparent from the further explanation.

In the situation disclosed in FIG. 1 a quantum of the liquid drug contained in the cartridge 5 has been filled into the cleaning chamber 51.

The cleaning chamber 51 is provided in a cleaning unit 50 which is carried by the distal shield part 40A. The cleaning chamber 51 is defined by a through-going opening in the cleaning unit 50 distally being sealed by a pierceable septum 52 and proximally closed by a rubber piston 53. This rubber piston 53 seals against the outer surface of the needle cannula 30.

The cleaning chamber 51 is preferably filled with the liquid drug from the cartridge 5 such that the same preservative containing liquid drug is present both inside the cartridge 5 and inside the cleaning chamber 51. However, the cleaning chamber 51 could alternatively be filled with a cleaning agent such as an alcohol.

When filling the cleaning chamber 51, the proximal rubber piston 53 moves proximally to the position disclosed in the figures. Alternatively, the proximal rubber piston 53 can be constructed as a septum in a permanent position in which case a valve is required to let the air out as the preservative containing liquid drug flows into the cleaning chamber 51.

The liquid system which comprises of the interior volume of the cartridge 5, the lumen 34 of the needle cannula 30 and the cleaning chamber 51 is relatively sensitive to pressure changes which can occur both when filling the cleaning chamber 51 and also afterwards especially due to temperature changes.

In order to obtain a correct dose expelling i.e. the number of units set by the user must in fact also be expelled during injection, it is necessary to equalize the pressure of the cartridge 5 with the pressure outside the liquid system prior to performing an injection.

Equalizing the pressure in the cartridge 5 is done by moving the distal tip 33 of the needle cannula 30 just outside the cleaning chamber 51 such that an overpressure inside the cartridge 5 (and inside the lumen 34 of the needle cannula 30) can escape.

In order to move the needle shield assembly 40 in the proximal direction to expose the tip 33 of the needle cannula 33, a rotatable ring 60 is in a first embodiment provided. This rotatable ring 60 is disclosed in details in FIG. 5 and comprises an outer serrated surface 61 and an internal helical track 62. This rotatable ring 60 is herein considered to be a part of the needle shield assembly 40.

The rotatable ring 60 is axially locked to the proximal shield part 40B which has a number of protrusions 44 (see FIG. 4) which engages the rotatable ring 60 e.g. by engaging behind the serrated surface 61. The rotatable ring 60 is thus rotatable in relation to the proximal shield part 40B but the rotatable ring 60 and the proximal shied part 40B are axially locked such that they move together in the axial direction.

Figure 6:
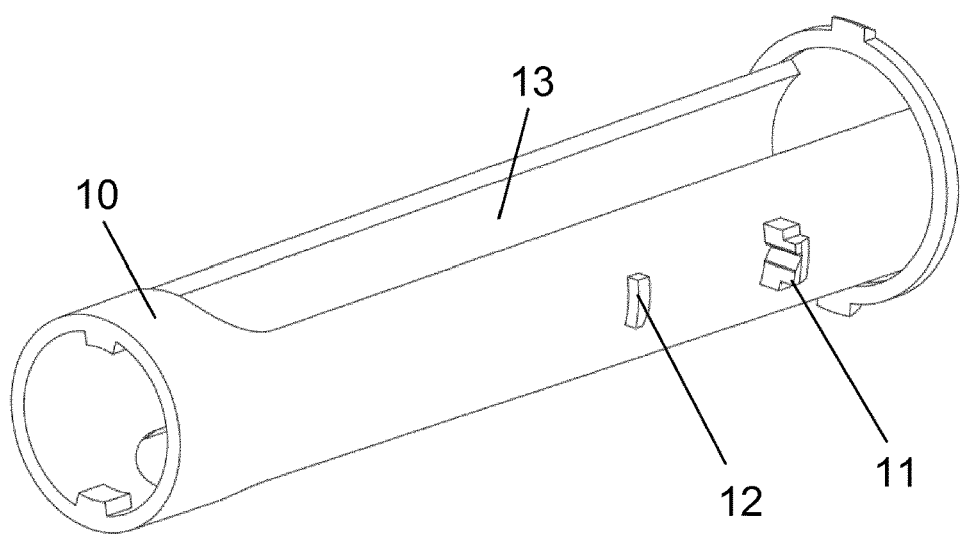
FIG. 6 show a perspective view of the cartridge holder.
Figure 7:
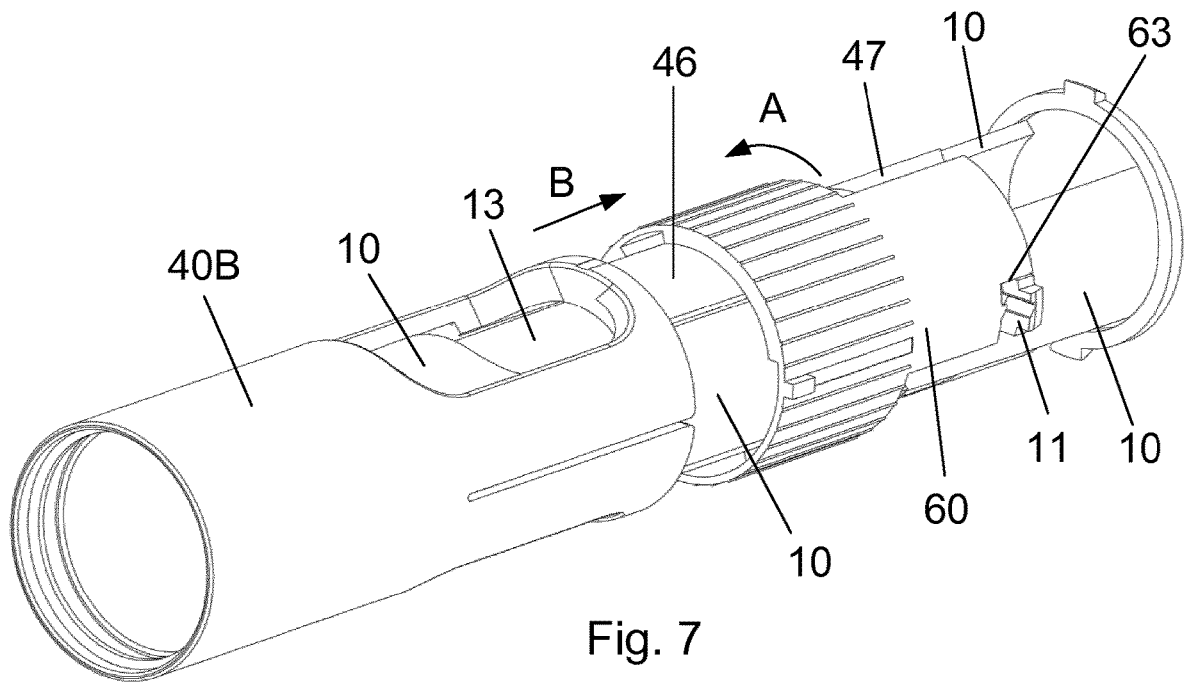
FIG. 7 show a perspective view of the engagement between part of the needle shield, the rotatable ring and the cartridge holder.

The cartridge holder 10 is depicted in FIG. 6 and comprises outwardly pointing protrusions 11 which secures the cartridge holder 10 to the housing 20. These outwardly pointing protrusions 11 also form rotational stops for the rotatable ring 60 by engaging a rotational stop surface 63 provided in the rotatable ring 60. In FIG. 7, the rotatable ring 60 is depicted in a parking position wherein the rotatable ring 60 axially abuts the protrusion 11 such that any axial movement of the needle shield assembly 40 is prevented. The cartridge holder 10 further has a protrusion formed as a thread segment 12 which engages a helical track 62 provided inside the rotatable ring 60 such that the rotatable ring 60 moves axially when rotated i.e. the rotational ring 60 performs a helical movement.

The helical track 62 terminates in an axial track 64 which allows the rotational ring 60 to move purely axially when the thread segment 12 is located in this axial track 64.

Figure 5:
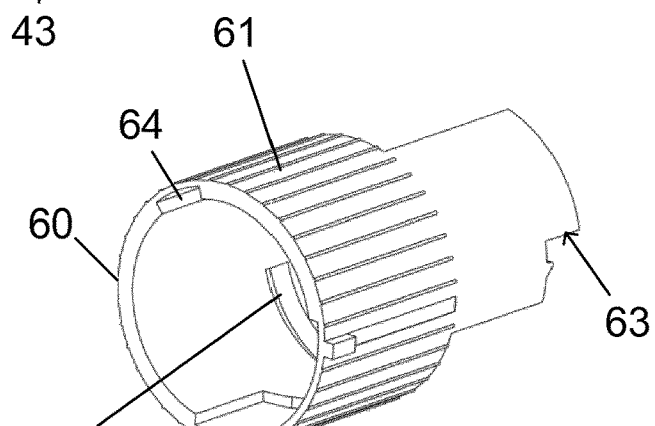
FIG. 5 show a perspective view of the rotatable ring.

As best seen in FIG. 1 and FIG. 5, the stop surface 63 of the rotatable ring 60 is provided on a proximal extension. In a preferred example, two such proximal extensions are provided each carrying a stop surface 63 which thus limits the angular rotation of the rotatable ring 60 to less than 180 degrees.

FIG. 7 discloses the cartridge holder 10, the proximal shield part 40B and the rotatable ring 60 together. In this shown example, the rotational stop surface 63 of the rotatable ring 60 engages one of the outwardly pointing protrusions 11. Further, the proximal extensions 46 are guided in longitudinal openings 13 provided in the cartridge holder 10 such that the proximal shield part 40B can only move axially without rotation.

The shield part 40B is further provided with a longitudinal extending window 39 such that a user can inspect the content of the cartridge 5 by looking through this longitudinal window 39 which is aligned with the longitudinal opening 13. Such window 39 is usually formed as an opening but can be covered by a well-known transparent material.

The rotatable ring 60 is thus axially locked to the proximal shield part 40B and helically guided by the thread segment 12 on the cartridge holder 10 which again is secured to the housing 20.

When a user rotates the rotatable ring 60 in the anti-clockwise direction as indicated by the arrow "A" in FIG. 7, this rotation forces the rotatable ring 60 to move helically in the proximal direction due to the thread segment 12 engaging the helical track 62 and since the proximal shield part 40B is axially coupled to the rotatable ring 60, the proximal shield part 40B moves axially in the proximal direction as indicated by the arrow "B" in FIG. 7.

Further, since the proximal shield part 40B and the distal shield part 40A is coupled together to operate as one needle shield assembly 40, the complete needle shield assembly 40 moves proximally into the position disclosed in FIG. 2 upon rotation of the rotatable ring 60.

As the rotatable ring 60 is rotated it also travels in the proximal direction together with the proximal shield part 40B. This is illustrated in FIG. 1 and FIG. 2.

As also seen in the FIGS. 1 to 3, the distal shield part 40A is at the end surface 42 provided with a concave recess 45 in which the distal tip 33 of the needle cannula 30 is positioned when the pressure is being equalized. In this way unnecessary physical contact with the distal tip 33 of the needle cannula 30 can be prevented.

After the pressure has been equalized an injection can be performed by pressing the distal surface 42 of the distal shield part 40A against the skin S. This axial movement of the distal shield part 40A will be conveyed to the proximal shield part 40B which will also move axially to the position disclosed in FIG. 3.

The helical track 62 leads to an axial track 64 allowing the rotatable ring 60 to move axially during injection as disclosed in FIGS. 2 and 3. As long as the thread segment 12 is located inside the helical track 62 only helical movement of the proximal shield part 40B is possible, however once the thread segment 12 is in the axial track 64 purely axial movement of the proximal shield part 40B is allowed.

The injection can either be performed as a shield-triggered injection i.e. a not-shown strained spring is released upon activation of the shield 40, or it can be a traditional injection in which the user needs to push a not-shown injection button. The activation of this not-shown injection button can in one example release a strained torsion spring which drives the piston rod 1 in the distal direction.

During axial movement of the needle shield assembly 40 in the proximal direction, the compression spring 55 will be compressed and once the injection is over and the distal surface 42 of the distal shield part 40A is removed from the skin S of the user, the compression spring 55 will urge the shield 40 in the distal direction to the position disclosed in FIG. 2. In order to transform to the first position depicted in FIG. 1, the user has to rotate the rotatable ring 60 in a clock-wise direction i.e. opposite the direction indicated by the arrow "A" in FIG. 7, or alternatively, the compression spring 55 has to supply a force sufficient to drive the thread segment 12 through the helical track 62.

In the end position, after injection and after the rotatable ring 60 has been rotated back, the distal tip 33 of the needle cannula 30 is once again positioned inside the cleaning chamber 51 and the protrusion 11 prevents any axial movement of the needle shield assembly 40

Figure 8:
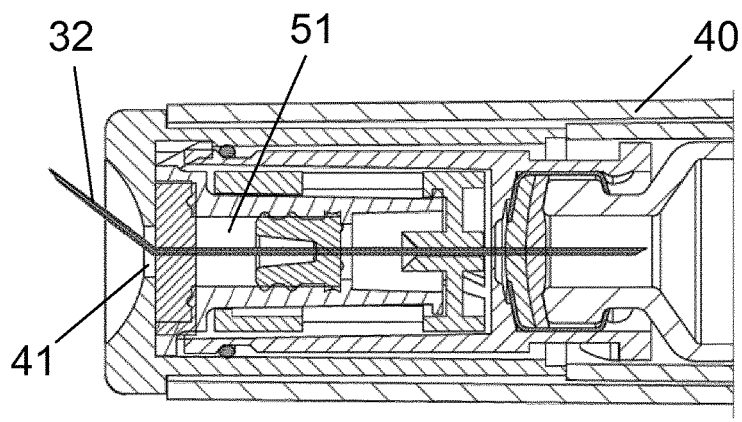
FIG. 8 show a cross sectional view of the distal part of the injection device with a damaged needle cannula.
Figure 9:
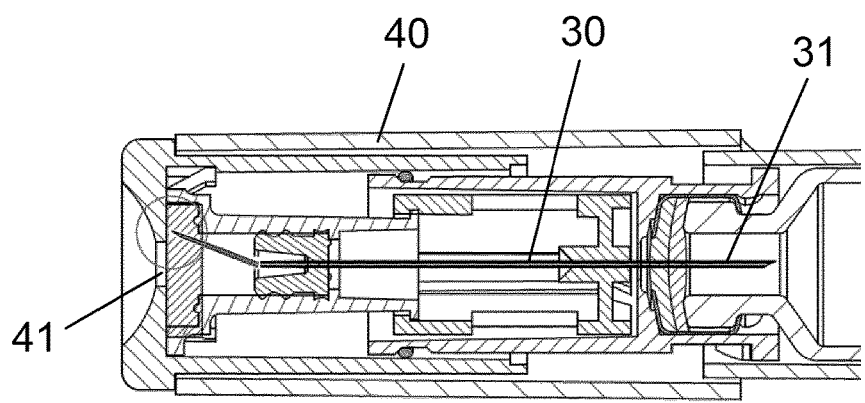
FIG. 9 show a cross sectional view of the distal part of the injection device with a damaged needle cannula and the needle shield in the first position.

Should the distal part 32 of the needle cannula 30 be bended or damaged during use as depicted in FIG. 8, the bended portion will enter into the cleaning chamber 51 as the needle shield assembly 40 I s moved back to its initial after injection. However, next time the user rotates the rotatable ring 60 to equalize the liquid system, the distal part 32 of the needle cannula 30 will remain bended to an off-centre position and the distal tip 33 of the needle cannula will abut the inside surface of the needle shield assembly 40 as disclosed in FIG. 9. This abutment will further damage e.g. break off the distal part 32 of the needle cannula 30 and prevent further injections. It is thus not possible to perform an injection with a bended needle cannula 30.

Obviously, the diameter of the opening 41 can be adjusted to accommodate the allowable degree of needle bend. This "needle trap" is usable in both the described embodiments.

Second Embodiment

A second embodiment is disclosed in the FIGS. 10 to 14. Similar parts have been indexed with the same numbers with a "1" in front. Thus the housing is numbered 120, the cartridge holder 110 and the needle shield assembly 140.

In the second embodiment, the needle shield assembly 140 comprises a distal shield part 140A and a proximal shield part 140B and there is no rotatable ring in the second embodiment. The two parts 140A, 140B could alternatively be moulded as one unitary part.

The distal shield part 140A carries the cleaning unit 150 having a cleaning chamber 151 which is either filled with the same preservative containing drug as present inside the cartridge 105 or with any different cleaning agent.

Figure 10:
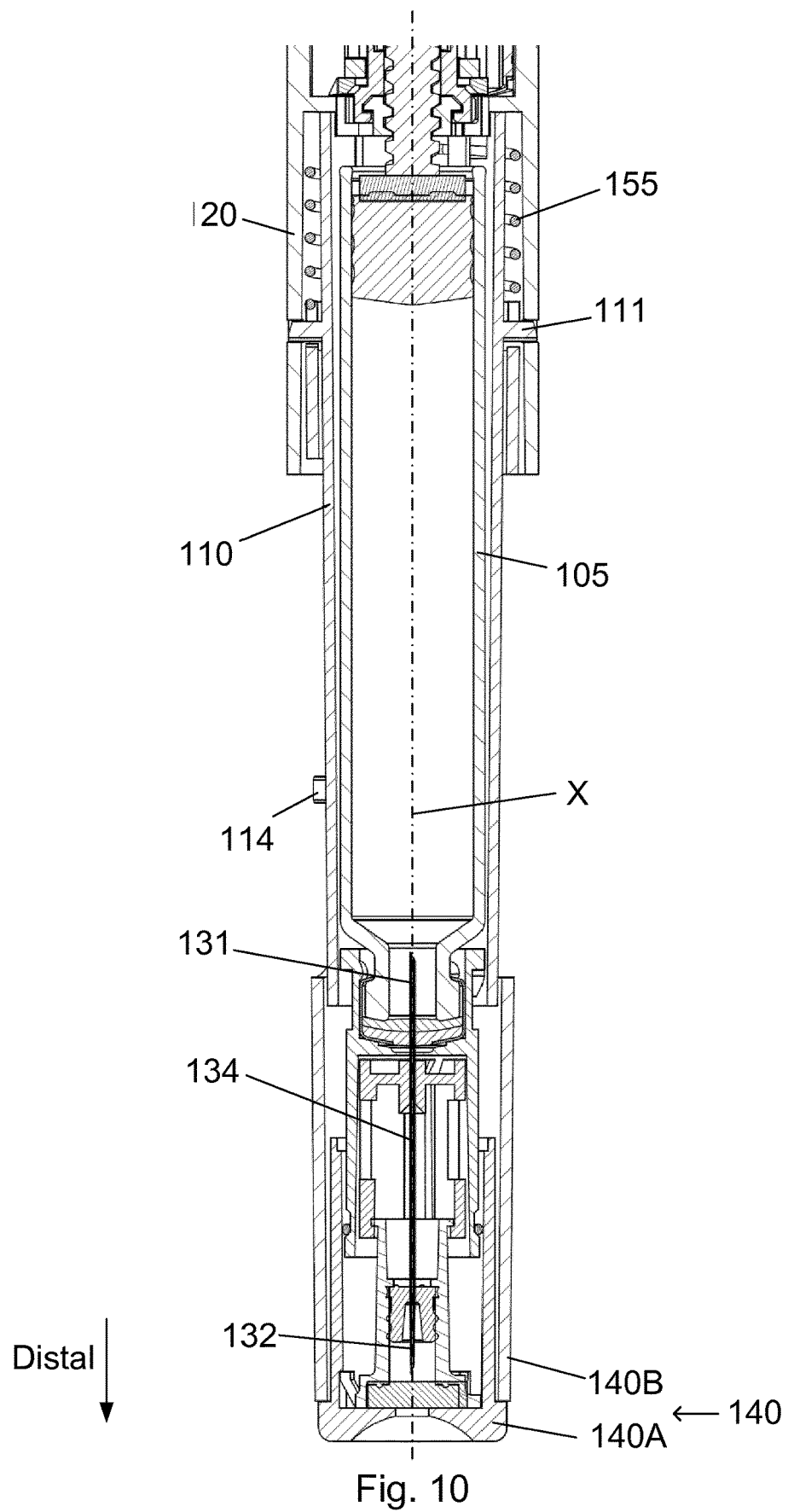
FIG. 10 show a cross sectional view of the distal part of the injection device according to another embodiment with the needle shield in the first position.

FIG. 10 discloses the injection device with the needle shield assembly 140 in the first position. Liquid drug has e.g. been filled from the cartridge 105 into the cleaning chamber 151 and as in the first embodiment the user must actively equalize the pressure before performing an injection.

FIG. 11 disclose the injection device with the needle shield assembly 140 in the second position and FIG. 12 disclose the injection device during injection of a dose.

As can be seen from the FIGS. 10 to 12, the needle shield assembly 140 distally carries the cleaning unit 150 which—as in the first embodiment—comprises a cleaning chamber 151 distally sealed by a pierceable septum 152 and proximally sealed by a sealing piston 153.

As in the first embodiment, the needle cannula 130 is secured in a hub 135 and the proximal part 131 is penetrated into the cartridge 105. The liquid system, in this second embodiment, also consist of the interior of the cartridge 105, the lumen 134 of the needle cannula 130 and the cleaning chamber 151.

In the second embodiment, the housing assembly 110, 120 comprises at least two parts, a regular housing 120 and a cartridge holder 110. The cartridge holder 110 is provided with a number of, preferably two, protrusions 111 for securing the cartridge holder 110 to the housing 120 to form one, at least operational, unit.

Figure 13:
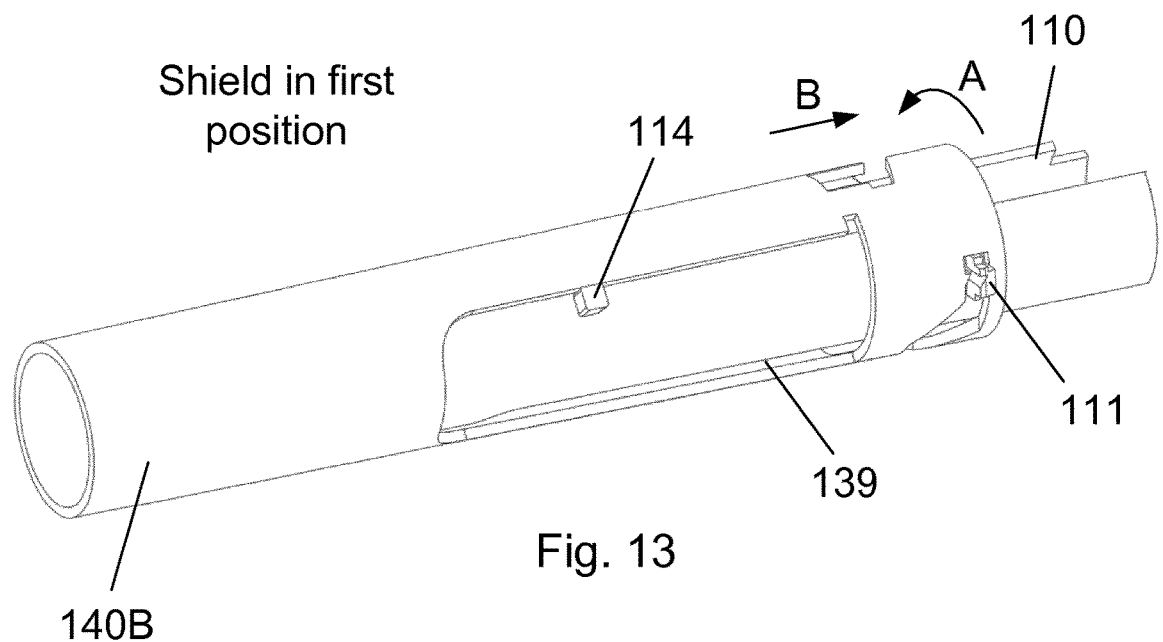
FIG. 13 show a perspective view of the engagement between part of the needle shield (in the first position) and the cartridge holder.
Figure 14:
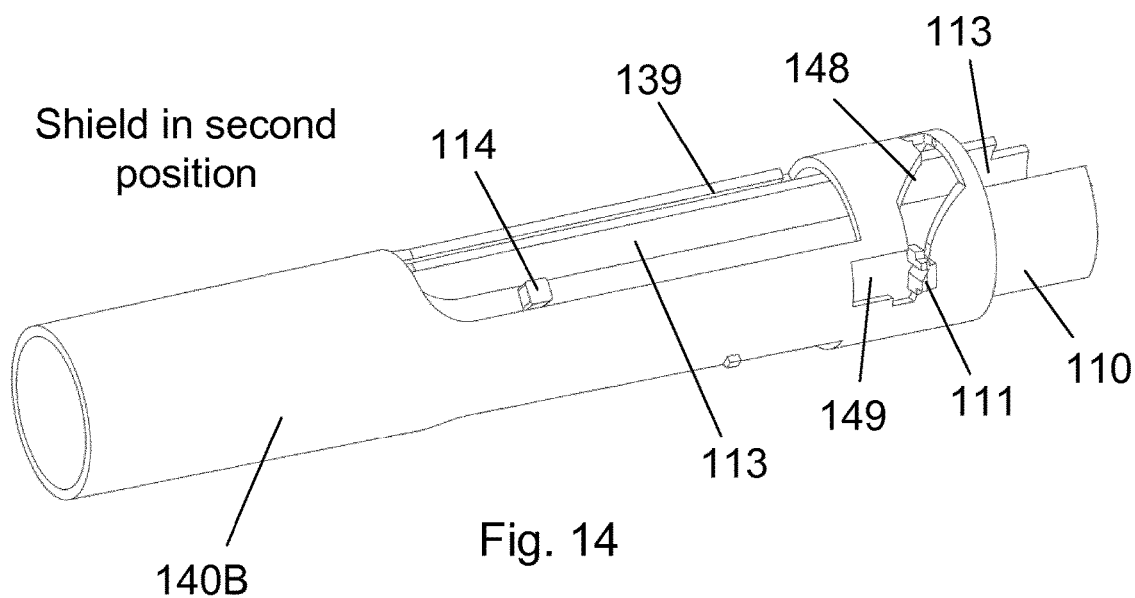
FIG. 14 show a perspective view of the engagement between part of the needle shield (in the second position) and the cartridge holder.

The corporation between the needle shield assembly 140 and the cartridge holder 110 is disclosed in FIGS. 13 and 14. As in the first embodiment, the distal shield part 140A and the proximal shield part 140B is both axially and rotational secured to each other.

The proximal shield part 140B of the needle shield assembly 140 is provided with a helical track 148 which is engaged by the outwardly pointing protrusion 111. This is best seen in FIG. 14. The result being that once the user rotate the needle shield assembly 140 counter clockwise (indicated by the arrow "A" in FIG. 13), the needle shield assembly 140 simultaneously travels in the proximal direction (as indicated by the arrow "B") in relation to the cartridge holder 110 thus performing a helical movement in relation to the housing assembly 110, 120.

The helical track 148 can as depicted in FIGS. 13 and 14 be provided with a radial extension making up the "parking position". When the protrusion 111 is positioned in this radial extension as depicted in FIG. 13 axial movement of the needle shield assembly 140 is prevented.

FIG. 13 depicts the situation of FIG. 10 wherein the needle shield assembly 140 is in the first extended position with the tip 133 of the needle cannula 130 inside the cleaning chamber 151. However, the cleaning unit 150 and the cleaning chamber 151 are not disclosed in FIG. 13 and FIG. 14.

As in the first embodiment, the needle shield assembly 140 is provided with a longitudinal window 139. When the pressure has not been equalized, this longitudinal window 139 is located above the solid part of the cartridge holder 10 such that the user cannot view the content of the cartridge 105.

Further, as in the first embodiment, the cartridge holder 110 is provided with longitudinal openings 113 such that the content of the cartridge 105 can be visually inspected when the longitudinal window 139 of the needle shield assembly 140 is aligned with the longitudinal opening 113 of the cartridge holder 110 forming part of the housing assembly 120, 110.

In the non-equalized position disclosed in FIG. 13, a protrusion 114 on the cartridge holder 110 abuts a first side of the longitudinal window 139 thus defining the possible rotational direction of the needle shield assembly 140.

Now, in order to equalize the pressure inside the cartridge 105, the user manually rotates the needle shield assembly 140 counter clock-wise (arrow "A") until the protrusion 114 provided on the cartridge holder 110 abuts the opposite side of the longitudinal window 139 in the needle shield assembly 140

Due to the rotation of the needle shield assembly 140 relatively to the housing assembly 120, 110, the needle shield assembly 140 moves helically in the proximal direction as the outwardly pointing protrusion 111 travels in the helical track 148 of the needle shield assembly 140

The needle shield assembly 140 simultaneously travels rotational as indicated by the arrow "A" and axially as indicted by the arrow "B" (FIG. 13), the combined movement thus being a helical movement.

When the outwardly pointing protrusion 111 arrives at the end of the helical track 148 as depicted in FIG. 14, the needle shield assembly 140 is in the equalizing position disclosed in FIG. 11 and the pressure has been equalized.

Once the needle shield assembly 140 has been moved to this second position (FIG. 11 and FIG. 14), the distal tip 133 of the needle cannula 130 is located just distal to the pierceable septum 152 but still within the parameters of the concave depression 145 at the distal end 142 of the distal shield part 140A. Further, in this position the outwardly pointing protrusion 111 is located in the longitudinal track 149 such that an injection can be performed as the shield 140 is now allowed to move purely proximally as depicted in FIG. 12.

As in the first embodiment, the distal shield part 140A is at the end surface 142 provided with a concave recess 145 in which the distal tip 133 of the needle cannula 30 is positioned when the pressure is being equalized i.e. when the needle shield assembly 140 is in the second position.

As the needle shield assembly 140 is rotated the longitudinal window 139 is brought into alignment with the longitudinal opening 113 of the cartridge holder 110. The possibility to view the cartridge 105 and thus the content of the cartridge 105 in the second, equalized, position is thus an indication to the user that the pressure has been equalized and an injection can be performed.

Further, in this second position depicted in FIG. 14 the needle shield assembly 140 is free to move in the proximal direction thus it is only possible to perform an injection after having rotated the needle shield assembly 140. The indication given by the alignment of the longitudinal window 139 with the longitudinal opening 113 is further an indication that the injection device is unlocked and ready to inject.

Some preferred embodiments have been shown in the foregoing, but it should be stressed that the invention is not limited to these, but may be embodied in other ways within the subject matter defined in the following claims.

The invention claimed is:

1. An injection device for injecting a liquid drug, comprising:
   a housing assembly supporting a non-removable cartridge having an interior chamber containing a liquid drug to be injected,
   a needle cannula connected to the cartridge and having a distal tip for penetrating the skin (S) of a user and a longitudinal lumen,
   a needle shield assembly which is provided with a cleaning chamber containing a volume of a cleaning agent for cleaning at least the distal tip of the needle cannula between subsequent injections, wherein
   the needle shield assembly is movable in a proximal direction in relation to the housing assembly from a first position to a second position, wherein;
   the first position is a position in which the distal tip of the needle cannula is located inside the cleaning chamber,
   the second position is a position in which the distal tip of the needle cannula is located outside and distal to the cleaning chamber for equalizing the pressure in the cartridge,
   wherein the at least one part of the needle shield assembly is helically guided in relation to the housing assembly, such that the at least one part of the needle shield assembly performs helical movement in relation to the housing assembly upon rotation of the at least one part of the needle shield assembly relatively to the housing assembly,
   and wherein the needle shield assembly moves from the first position to the second position thereby exposing at least the distal tip of the needle upon rotation of at least one part of the needle shield assembly.

2. An injection device for injecting a liquid drug according to claim 1, wherein one of the needle shield assembly or the housing assembly is provided with a protrusion and the other of the needle shield assembly or the housing assembly is provided with a helical track, and wherein the protrusion engages the helical track, such that the at least one part the needle shield assembly moves helically in relation to the housing assembly upon rotation of the at least one part of the needle shield assembly relatively to the housing assembly.

3. An injection device for injecting a liquid drug according to claim 2, wherein the helical track terminates in an axial track allowing the needle shield assembly to be moved in the proximal direction during expelling of a set dose.

4. An injection device for injecting a liquid drug according to claim 1, wherein a compression spring is operational between the needle shield assembly and the housing assembly urging the needle shield assembly in the distal direction.

5. An injection device for injecting a liquid drug according to claim 1, wherein the needle shield assembly comprises at least a distal shield part and a proximal shield part rotatable in unison.

6. An injection device for injecting a liquid drug according to claim 1, wherein the needle shield assembly comprises a rotatable ring.

7. An injection device for injecting a liquid drug according to claim 6, wherein the rotatable ring is rotatable in relation to the proximal shield part and axially secured to the distal shield part.

8. An injection device for injecting a liquid drug according to claim 7, wherein one of the rotatable ring or the housing assembly is provided with a protrusion and the other of the rotatable ring or the housing assembly is provided with a helical track, such that the rotatable ring moves helically in relation to the housing assembly upon rotation of the rotatable ring relatively to the housing assembly.

9. An injection device for injecting a liquid drug according to claim 1, wherein the needle shield assembly or the housing assembly is provided with a protrusion and the other of the needle shield assembly or the housing assembly is provided with a helical track such that the needle shield assembly moves helically in relation to the housing assembly upon rotation of the needle shield assembly relatively to the housing assembly.

10. An injection device for injecting a liquid drug according to claim 9, wherein the needle shield assembly is provided with a window and the housing assembly is provided with an opening and which window is brought into alignment with the opening when the needle shield assembly is rotated relatively to the housing assembly.

11. An injection device for injecting a liquid drug according to claim 1, wherein the needle shield assembly carries a cleaning unit comprising the cleaning chamber.

12. An injection device for injecting a liquid drug according to claim 1, wherein the cleaning agent contained in the cleaning chamber is the same liquid drug as contained in the cartridge and wherein the liquid drug comprises a preservative.

13. An injection device for injecting a liquid drug according to claim 1, wherein the needle shield assembly distally is provided with a distal surface having an opening surrounded by a recess.

14. An injection device for injecting a liquid drug according to claim 13, wherein the distal tip of the needle cannula in the second position is positioned in the recess.

* * * * *